(12) United States Patent
Truesdell

(10) Patent No.: US 6,180,375 B1
(45) Date of Patent: Jan. 30, 2001

(54) MICROBIAL BIOTRANSFORMATION

(75) Inventor: Susan J. Truesdell, Warwick, RI (US)

(73) Assignee: Pfizer Inc., New York, NY (US)

( * ) Notice: Under 35 U.S.C. 154(b), the term of this patent shall be extended for 0 days.

(21) Appl. No.: 09/384,924

(22) Filed: Aug. 27, 1999

(51) Int. Cl.$^7$ .................................................. C12P 17/18
(52) U.S. Cl. ............................................................. 435/121
(58) Field of Search ............................................. 435/121

(56) References Cited

U.S. PATENT DOCUMENTS 4,431,736 * 2/1984 Romesser ............................ 435/911

OTHER PUBLICATIONS

Computer Abstract Scisearch Sedlaczek Et Al "Oxidation–Reduction State of the Nicotinamide Nucleotides and the Steroid 11–Alpha Hyudroxylase Activity in *Monosporium olivaceum* ATCC–36300" ACTA Microbio. Polonica (1979) vol. 28. No. 2 pp. 111–121, 1979.*
Computer Abstract Caplus Rosati Et Al "Discovery and SAR of a Potent Non–Steroidal Estrogen Agonist, CP–336, 156" ABS 212 ACS Meeting ORL FLOR (1996).*
Computer Abstract Biosis AN1996:491867 Ke Et Al "CP–336, 156, A New Estrogen Agonist/Antagonist, Inhibits Bone Turnover and Prevents Bone Loss in Ovariectomized Rats" Bone (New York) (1996) vol. 19 No. 3 Suppl PP 145 S, 1979.*

* cited by examiner

*Primary Examiner*—Herbert J. Lilling
(74) *Attorney, Agent, or Firm*—Peter C. Richardson; Paul H. Ginsburg; Robert F. Sheyka

(57) ABSTRACT

The present invention relates to the use of microorganisms of the Monosporium and Thamostylum genera to diastereoselectively O-demethylate pharmaceutical intermediates, to produce compounds of the formulae:

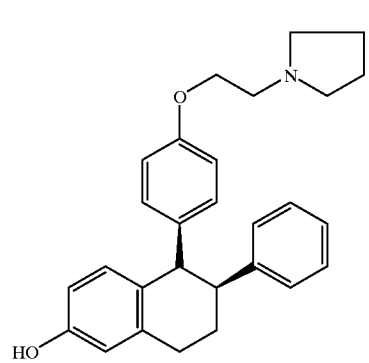

I

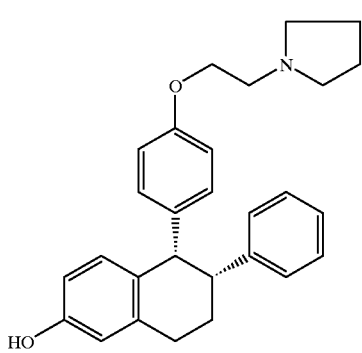

III

6 Claims, 4 Drawing Sheets

MICROBIAL BIOTRANSFORMATION

This application claims priority from U.S. Provisional Application Ser. No. 60/098,255 filed on Aug. 28, 1998.

BACKGROUND OF THE INVENTION

The present invention is directed to the use of microbial biotransformation to O-demethylate certain pharmaceutical intermediate compounds. More specifically, it is directed to the use of certain microoganisms to O-demethylate certain pharmacetical intermediate compounds.

An article in Analytica Chimica Acta(1990) 233, 191–198 refers to the use of *Cunninghamella elegans* to demethylate certain n-propylnoraporphine compounds.

An article in Biomedical and Enviromental Mass Spectrometry (1986) 13, 223–229 refers to the use of *Cunninghamella elegans* to produce potential metabolites of N-n-propyl norapo morphine.

A review article published in Enzyme and Microbial Technology (1984) 6,242–253 at pages 250–252 broadly reviews the use of certain microorganisms, e.g. fungal species such as Cunninghamella, Aspergillus, Thamnostylum, Penicillium and Sepedonium to O-dealkylate certain compounds.

Chapter 5.5 of Biotransformations in Preparative Organic Chemistry by H. G. Davies et al refers to the use of *Sepedonium chrysospermum* and *Cunninghamella elegans* to demethylate certain compounds, including vindoline and 10,11-dimethoxyaporphine.

An article in Phytochemistry (1997) 44 (8), 1479–1482, refers to the use of *Aspergillus niger* to produce (−)-pinoresinol through O-demethylation of (±)-eudesmin.

U.S. Pat. No. 5,618,707 granted Apr. 18, 1997 refers to the use of *Zygosaccharomyces bailii* ATCC 38924 to stereoselectively reduce a pentanoic acid compound to a phenyloxazolidinone product.

U.S. Pat. No. 5,580,764 refers to the use of oxido/reductases from *Lactobacillus plantarum, Pichia haplophila, Candida utilis, Lactobacillus buchmans, Aspergillus flavus* and *Neurospora crassa* to reduce intermediates in the synthesis of carbonic anhydrase inhibitors.

SUMMARY OF THE INVENTION

In one embodiment, the present invention is directed to a process for the production of a compound of the formula:

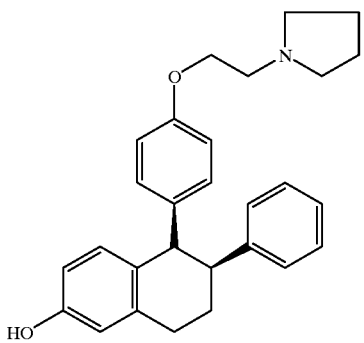

from a compound of the formula

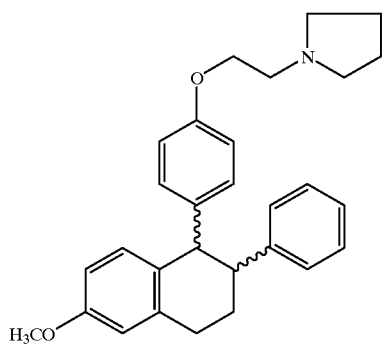

comprising selectively demethylating a compound of formula II in the presence of an enzyme derived from a culture of a microorganism of the genus Monosporium.

Preferred is the process wherein said microorganism is *Monosporium olivaceum*.

Also preferred is the process wherein said *Monosporium olivaceum* is *Monosporium olivaceum* ATCC 36300.

In another embodiment, the present invention is directed to a process for the preparation of a compound of the formula

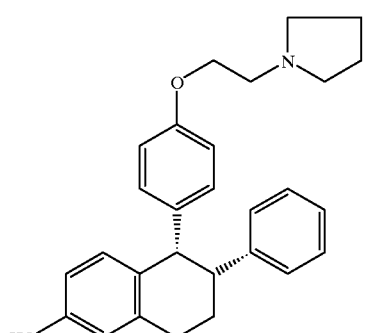

from a compound of the formula

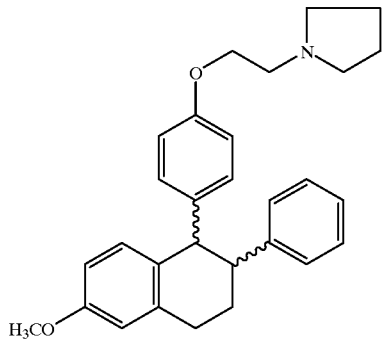

II comprising selectively demethylating a compound of formula II in the presence of an enzyme derived from a microorganism of the genus Thamnostylum.

Preferred is the process wherein said microorganism is *Thamnostylum piriforme*.

Also preferred is the process wherein said *Thamnostylum piriforme* is *Thamnostylum piriforme* ATCC 8992.

In another embodiment, the present invention is directed to the use of a compound of the formula

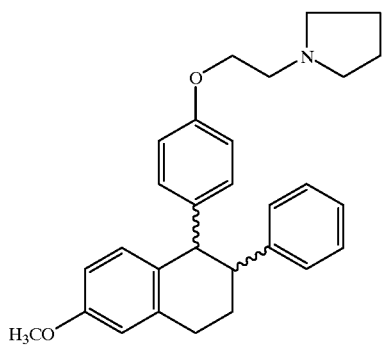

II to produce a compound of the formula

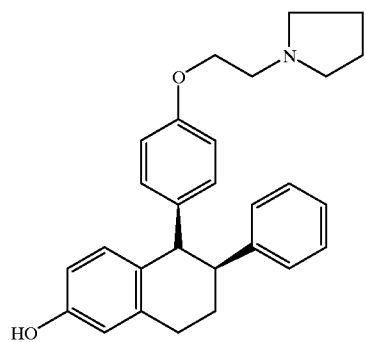

I

Preferred is the use wherein a compound of formula II is non-selectively demethylated.

DETAILED DESCRIPTION OF THE INVENTION

This invention comprises using microorganisms to effect O-demethylation of an intermediate in the synthesis of CP-336,156 (estrogen agonist/osteoporosis). Use of microbes eliminates the chemical step which produces methyl bromide, a greenhouse gas which is difficult and expensive to trap, as a byproduct.

The biotransformation may be carried out using whole cell cultures of the micoorganisms, cell extracts of the microorganisms, or purified enzymes from the microorganisms The starting material for this microbial biotransformation is CP-324,098, which is a mixture of the cis diastereomers. Three fungi have been found which carry out this reaction with different stereoselectivities. *Cunninghamella echinulata* O-demethylates both diastereomers to form the racemic mixture named CP-319,609, which is comprised of the diastereomers CP-5,336,156 and CP-335,992. *Monosporium olivaceum* and Thamnostylum piriforme act on only one of the diastereomers in CP-324,098 and yield a single diastereomer product as indicated below.

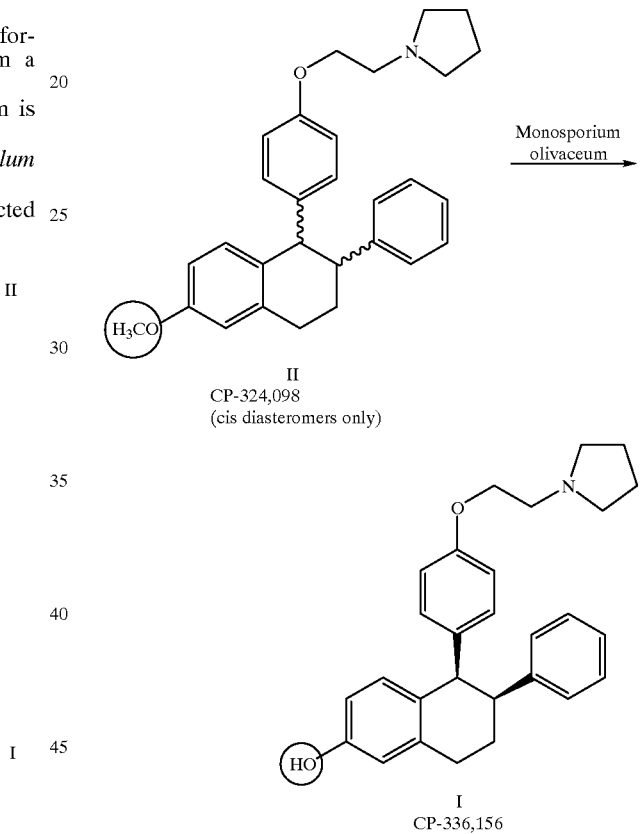

Figure 1:
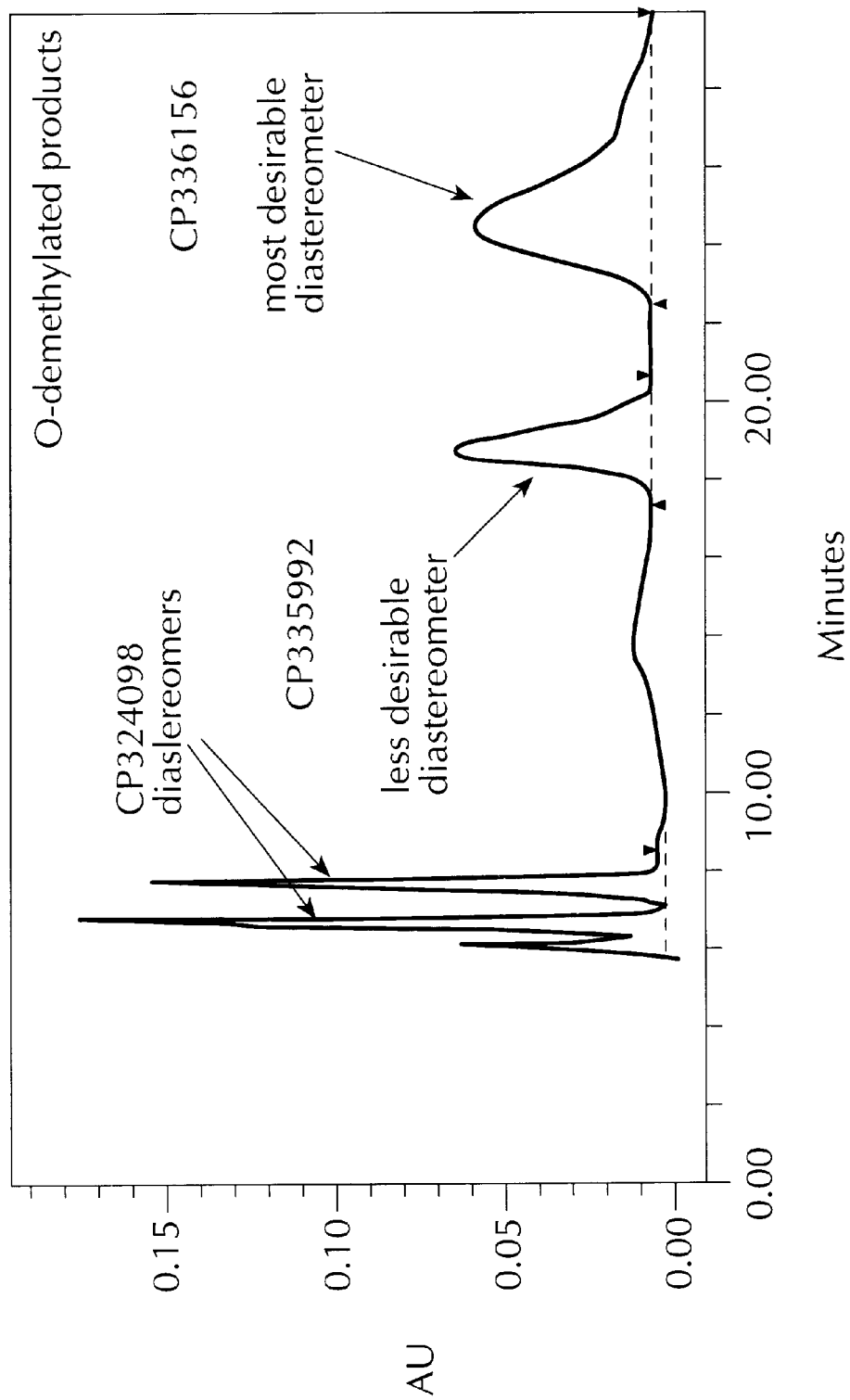
FIGS. 1–4 illustrate High Pressure Liquid Choromatography profiles generated using microbial biotransformation by 3 fungal cultures.
Figure 2:
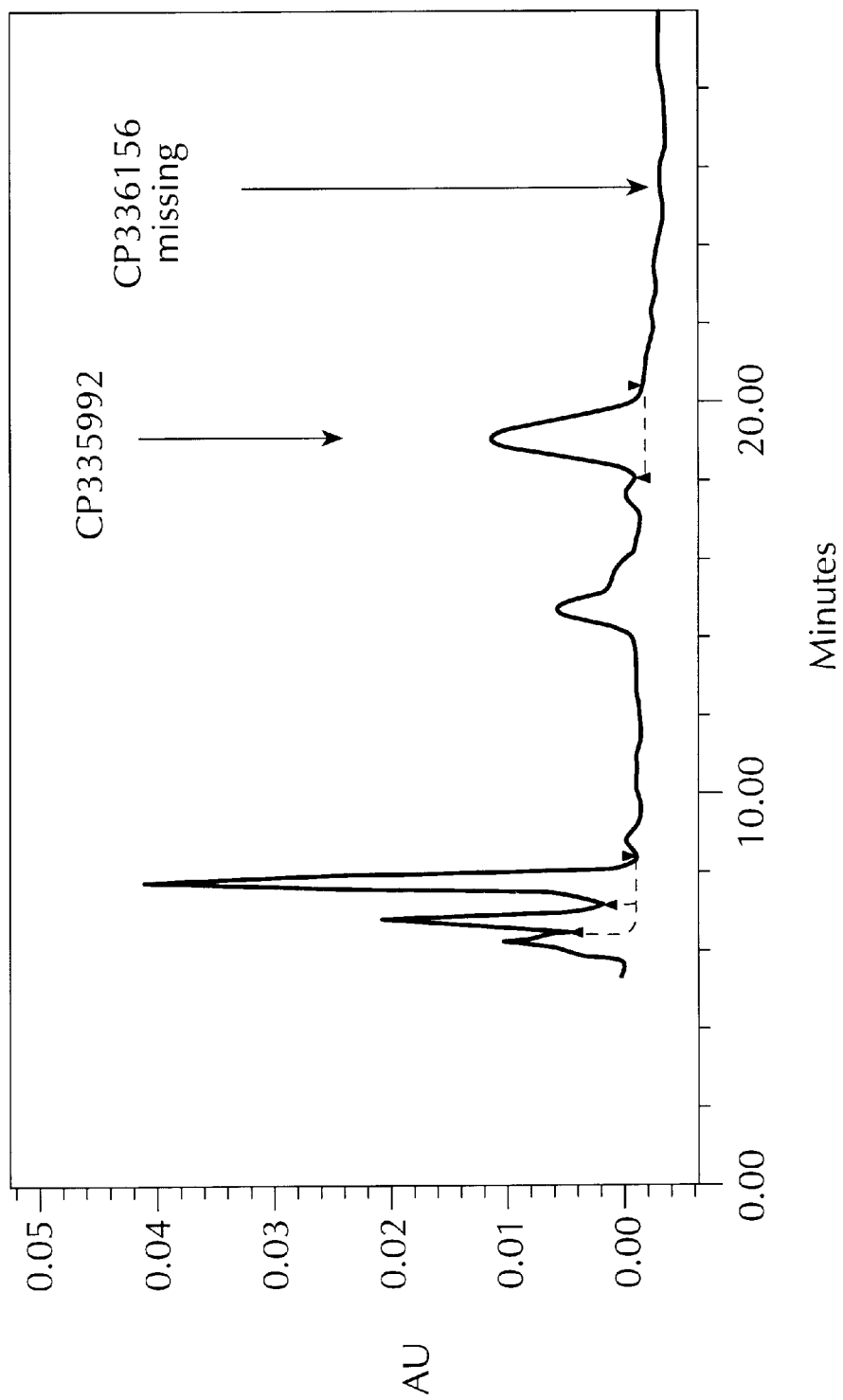
Figure 3:
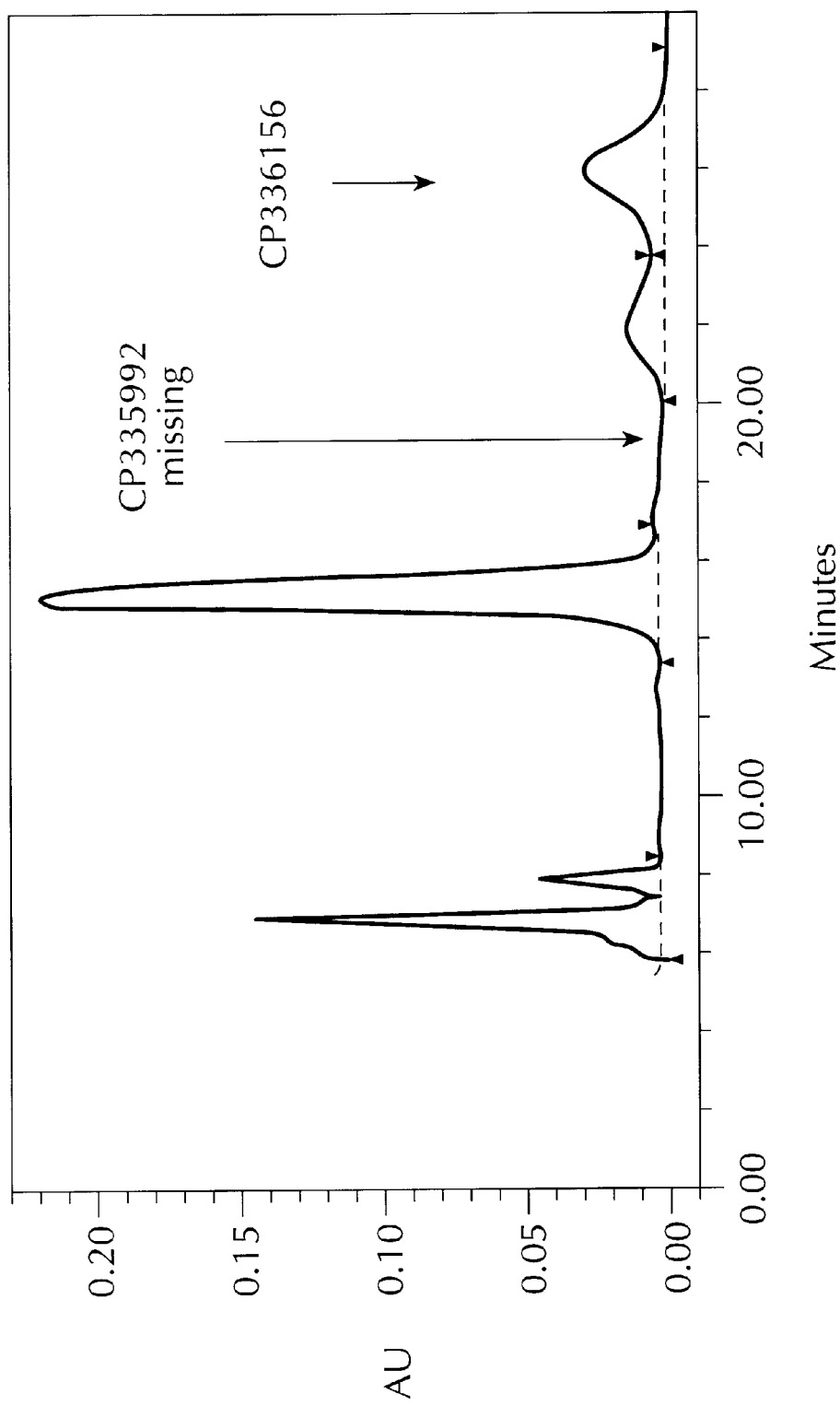
Figure 4:
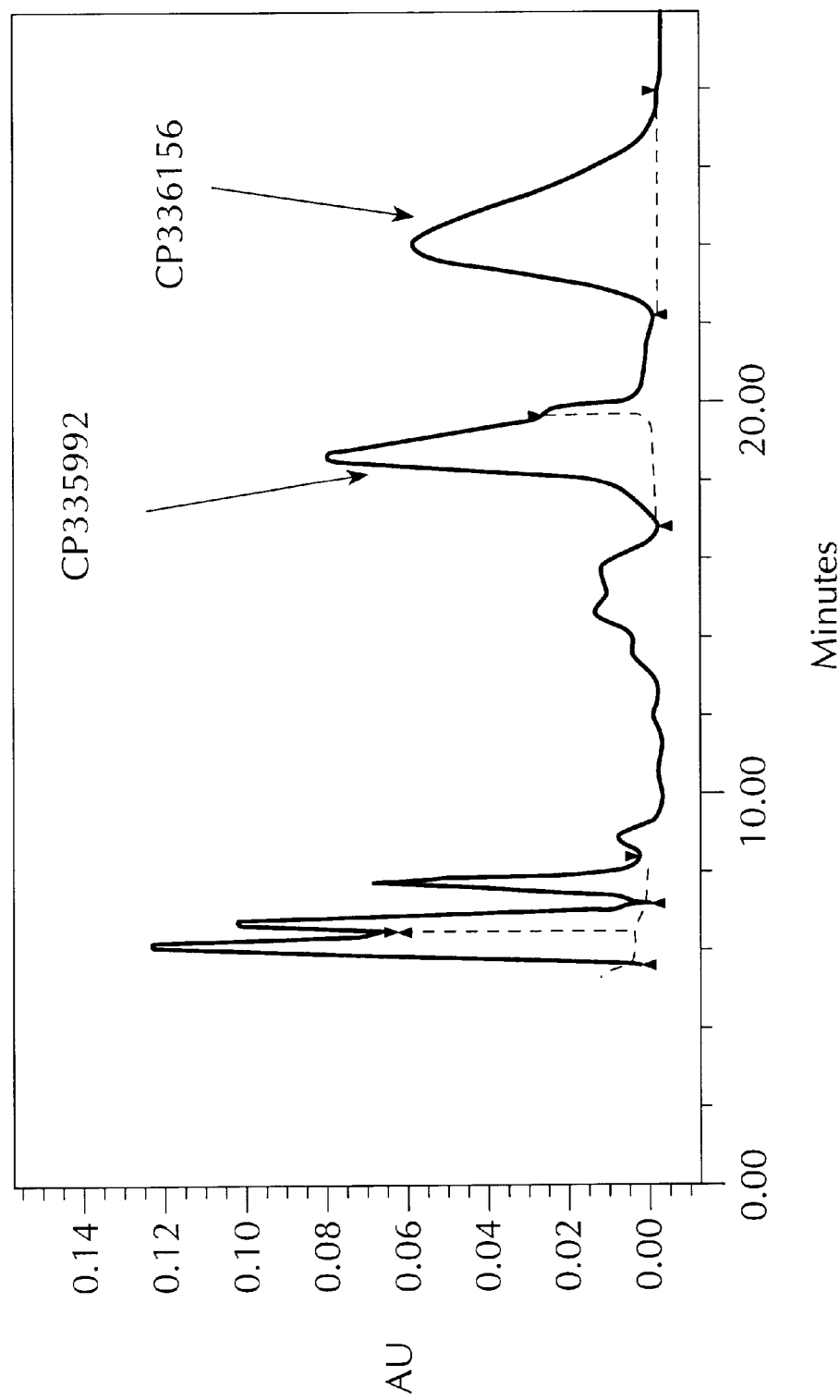

The starting material and the products made by these three organisms were determined by chiral HPLC as shown in FIGS. 1–4. The final products of the reactions of all three microorganisms were isolated from the fementation broth and characterized by NMR MS, and chiral HPLC to confirm their identity Having described the invention in general terms, reference is now made to specific examples. It is to be understood that these examples are not meant to limit the present invention, the scope of which is determined by the appended claims Monosporium olivaceum ATCC 36300 and Thamnostylum piriforme ATCC 8992 can be obtained from the American Type Culture Collection. A culture so obtained is added to a suitable growth medium and is incubated with shaking until growth occurs. The cultures thus prepared are used to inoculate slants. Portions of these slants are frozen as master stocks. The respective microorganisms are inoculated from slants into two flasks containing a growth medium whose composition is shown below. The fermentation is carried out at temperatures ranging from about 22 to about 32; however, for optimum results it is preferable to conduct the fermentation at about 28. The pH of the medium is controlled at about pH 6–7 by the use of suitable organic or inorganic buffers incorporated into the fermentation medium or by periodic addition of a base. Good growth of the microorganism is achieved within 48 to 72 hours. The contents of the flasks are transferred to a Fernbach flask containing fresh growth medium having the same composition as the previously used growth medium. Variation of the medium will alter the yield of the compound and its rate of production. The preferred media composition is set forth in the example section. After shaking for one additional day, a sterile-filtered solution of rapamycin in a suitable solvent such as dimethyl sulfoxide or dimethylformamdide is added. The fermentation is continued for one to six days. It is preferred to continue the fermentation for about two days.

A suitable growth medium for use in the process of this invention will contain a source or sources of assimilable carbon, assimilable nitrogen and inorganic salts containing essential minerals. In general, many carbohydrates such as glucose, maltose, mannose, sucrose, starch, glycerin, millet jelly, molasses, soy bean and the like can be used as sources of assimilable carbon. Sources of assimilable nitrogen include such materials as yeast and casein hydrolysates, primary yeast, yeast extracts, cottonseed flour, soybean solids, wheat germ meat extracts, peptone, corn steep liquor, and ammonium salts. The inorganic salt nutrients which can be incorporated in the culture medium are the customary salts yielding sodium, iron, magnesium, potassium, cobalt, phosphate and the like. In general, of course, the techniques employed and are not intended to be limiting.

Suitable grow media include (a) dextrose (20 g), yeast extract (5 g), soy flour (5 g), NaCl (5 g), $K_2HPO_4$ (5 g) and distilled water (1000 milliliters) where the pH is adjusted to 7.0 with aqueous HCl; (b) dextrin (10 g), beef extract (3 g), ardamine pH (5 g), N-Z amine type E (5 g), $MgSO_4 7H_2O$ (0.,5 g), $KH_2PO_4$ (0.37 g), $CaCO_3$ (0.5 g), distilled water (1000 milliliters) where the pH is adjusted to 7.1 with aqueous HCl followed by a second stage of glucose (10 g), Hy-Case SF (2 g), beef extract (1 g), corn steep liquor (3 g), distilled water (1000 milliliters) where the pH is adjusted to 7.0; (c) glucose (10 g), corn step liquor (6 g), $KH_2PO_4$ (3 g), $CaCO_3$ (3.5 g), Soybean oil (crude, 2.2 milliliters), yeast extract (2.5 g), distilled water (1000 milliliters) where the pH is adjusted to 7.0–7.3 with aqueous HCl; (d) malt syrup (20 g), soybean mean (5 g), casein (1 g), dried yeast (1 g), NaCl (5 g), distilled water (1000 milliliters); (e) lactose (75 g), Pharmamedia (substitute yeast extract, 40 g), $CaCO_3$ (10 g), $Na_2SO_3$ (4 g), distilled water (1000 milliliters); (f) ISP #3; (h) ISP#4; (I) ISP#5 and the like.

Procedures

Cultures: *Cunninghamella echinulata* ATCC 9244 and ATCC 36190; *Monosporium olivaceum* ATCC 36300 and *Thamnostylum piriforme* ATCC 8992.

Biotransformation

Growth medium (inoculum & biotransformation stages):

| | | |
|---|---|---|
| glucose | 20 g/l | pH to 7.0 |
| soy flour or soy meal | 5 | |
| yeast extract | 5 | |
| NaCl | 5 | |
| $K_2HPO_4$ | 5 | |

25 ml per 125 ml Erlenmeyer flask for inoculum and biotransformation. Inoculate from slants or frozen stock cultures into 25 ml of the medium above in a 125 ml Erlenmeyer flask and incubate with shaking at 28° C. for 2–3 days. Transfer 2.5 ml into 25 ml of fresh broth in an Erlenmeyer flask and shake another day. Add CP-324,098 dissolved in DMSO and filter sterilized to a final concentration of 0.2 mg/ml. Additional substrate can be fed at 1 day intervals. Continue incubation with shaking for 1–6 days.

Extraction and Purification

Broth was extracted with twice its volume of ethyl acetate in a separatory funnel. The phases were separated by centrifugation at 1000×g for 5 minutes after which the upper ethyl acetate phase was carefully removed and evaporated to dryness. Methanol also works well as an extraction solvent. The product can be purified using solid phase extraction and preparative HPLC.

Chiral HPLC Assay

| | |
|---|---|
| Column | Chiral OD, 4.6 × 250 mm (Daicel, Chiral Technologies) |
| Flow Rate | 0.7 ml/min |
| Sample Size | 20 µl |
| Concentration | 0.1 mg/ml |
| Temperature | 30° C. |
| Detection | UV at 220 nm |
| Mobile Phase | 100 ml ethyl alcohol (USP, dehydrated, 200 proof) plus 900 ml hexane plus 1 ml N'N'-diethyl amine |

Samples are dissolved in ethanol

What is claimed is:

1. A process for the production of a compound of the formula:

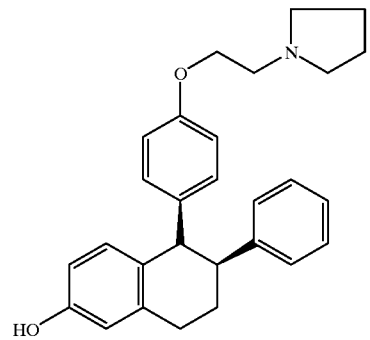

I from a compound of the formula:

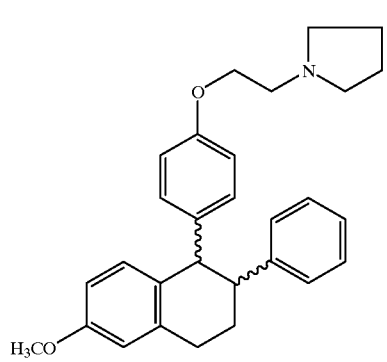

II comprising selectively demethylating a compound of formula II in the presence of an enzyme contained in a culture of a microorganism of the genus Monosporium.

2. A process according to claim 1 wherein said microorganism is *Monosporium olivaceum*.

3. A process according to claim 2 wherein said *Monosporium olivaceum* is *Monosporium olivaceum* ATCC 36300.

4. A process for the production of a compound of the formula:

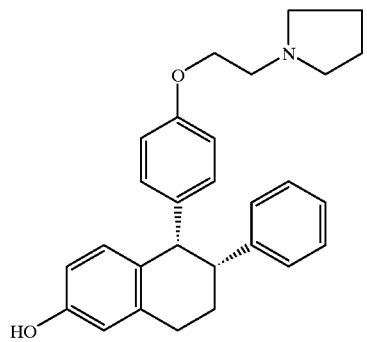

from a compound of the formula

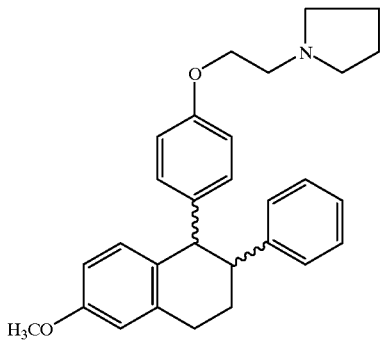

comprising selectively demethylating a compound of formula II in the presence of an enzyme contained in a culture of a microorganism of the genus Thamnostylum.

5. A process according to claim 4 wherein said microorganisms is *Thamnostylum piriforme*.

6. A process according to claim 5 wherein said Thamnostylum is *Thamnostylum piriforme* ATCC 8992.

* * * * *